(12) United States Patent
Kendrick et al.

(10) Patent No.: US 12,053,593 B2
(45) Date of Patent: Aug. 6, 2024

(54) WETTING MECHANISM FOR A CATHETER

(71) Applicant: CONVATEC LIMITED, Flintshire (GB)

(72) Inventors: Andrew Kendrick, Cheshire (GB); Julie Lambrethsen, Cheshire (GB); Oliver Walter Pfleger, Merseyside (GB); Michal Weber, Cheshire (GB)

(73) Assignee: CONVATEC LIMITED, Flintshire (GB)

( * ) Notice: Subject to any disclaimer, the term of this patent is extended or adjusted under 35 U.S.C. 154(b) by 322 days.

(21) Appl. No.: 17/238,697

(22) Filed: Apr. 23, 2021

(65) Prior Publication Data

US 2021/0330938 A1 Oct. 28, 2021

Related U.S. Application Data

(63) Continuation of application No. PCT/GB2021/050983, filed on Apr. 23, 2021.

(30) Foreign Application Priority Data

Apr. 24, 2020 (GB) ...................... 2006060

(51) Int. Cl.
*A61M 25/00* (2006.01)
*A61M 25/01* (2006.01)

(52) U.S. Cl.
CPC ...... *A61M 25/0075* (2013.01); *A61M 25/002* (2013.01); *A61M 25/0111* (2013.01);
(Continued)

(58) Field of Classification Search
CPC ............ A61M 25/0075; A61M 25/002; A61M 2025/0078; A61M 2202/0496;
(Continued)

(56) References Cited

U.S. PATENT DOCUMENTS 3,805,770 A * 4/1974 Okada .................. A61B 1/31
D24/138
3,871,358 A * 3/1975 Fukuda .............. A61B 1/00154
600/585

(Continued)

FOREIGN PATENT DOCUMENTS

AU 2014360561 B2 6/2015
CA 3173669 A1 9/2021
(Continued)

OTHER PUBLICATIONS

International Search Report; European Patent Office; International Application No. PCT/GB2021/050983; Aug. 10, 2021; 4 pages.

(Continued)

*Primary Examiner* — Adam Marcetich
(74) *Attorney, Agent, or Firm* — TAFT STETTINIUS & HOLLISTER LLP; Ryan O. White; Derek B. Lavender

(57) ABSTRACT

The invention relates to a wetting mechanism 20 for wetting a tube 12 of a catheter 10. The wetting mechanism 20 includes a housing 16 positioned initially at or proximal to the tip end 13 of the catheter tube 12. The housing 16 comprises a wetting chamber 23 into which at least a portion of the catheter tube 12 is able to be introduced and be moved therethrough to wet the catheter tube 12 in use. The wetting mechanism 20 includes a wetting applicator 40 positioned within the wetting chamber 23 configured to hold fluid therein and release said fluid to wet the catheter tube 12 upon movement of the tube 12 through the wetting chamber 23.

20 Claims, 7 Drawing Sheets

(52) U.S. Cl.
CPC . *A61M 25/0113* (2013.01); *A61M 2025/0078* (2013.01); *A61M 2202/0496* (2013.01); *A61M 2210/167* (2013.01)

(58) Field of Classification Search
CPC ........ A61M 2210/167; A61M 25/0111; A61M 25/0017; A61M 25/0113
See application file for complete search history.

(56) References Cited

U.S. PATENT DOCUMENTS

| | | | |
|---|---|---|---|
| 3,898,993 A * | 8/1975 | Taniguchi | A61M 25/0111 604/172 |
| 4,834,711 A * | 5/1989 | Greenfield | A61M 25/0111 604/172 |
| 5,941,815 A * | 8/1999 | Chang | A61B 1/31 600/114 |
| 6,554,808 B1 * | 4/2003 | Cook | A61M 25/09041 604/265 |
| 11,376,395 B2 | 7/2022 | Montes de Oca et al. | |
| 11,420,016 B2 | 8/2022 | Palmer | |
| 11,420,017 B2 | 8/2022 | Hilton et al. | |
| 11,497,886 B2 | 11/2022 | Nielsen et al. | |
| 11,524,097 B2 | 12/2022 | Sellers et al. | |
| 11,529,439 B2 | 12/2022 | O'Mahony | |
| 11,534,573 B2 | 12/2022 | Hannon et al. | |
| 11,534,577 B2 | 12/2022 | House | |
| 11,690,947 B2 | 7/2023 | Gobel | |
| 11,724,008 B2 | 8/2023 | Lundahl et al. | |
| 11,730,557 B2 | 8/2023 | O'Flynn et al. | |
| 11,730,918 B2 | 8/2023 | Farrell et al. | |
| 11,738,169 B2 | 8/2023 | Hickmott et al. | |
| 11,771,584 B2 | 10/2023 | Becker | |
| 11,813,412 B2 | 11/2023 | O'Flynn et al. | |
| 11,833,274 B2 | 12/2023 | Rostami et al. | |
| 2003/0018302 A1 * | 1/2003 | Kavanagh | A61M 25/002 604/171 |
| 2007/0088330 A1 * | 4/2007 | House | A61M 25/0111 604/327 |
| 2008/0051630 A1 | 2/2008 | Levey et al. | |
| 2008/0097463 A1 * | 4/2008 | House | A61M 25/002 606/108 |
| 2009/0112054 A1 * | 4/2009 | Lindberg | A61M 35/003 600/38 |
| 2011/0230864 A1 * | 9/2011 | House | A61M 25/0111 604/544 |
| 2012/0110951 A1 * | 5/2012 | van Groningen | A61M 25/0111 53/425 |
| 2016/0022959 A1 | 1/2016 | Schertiger et al. | |
| 2016/0213880 A1 * | 7/2016 | O'Flynn | A61M 25/0111 |
| 2016/0339205 A1 * | 11/2016 | Foley | A61M 27/00 |
| 2018/0078700 A1 | 3/2018 | Eliasson | |
| 2018/0099318 A1 * | 4/2018 | Wiwi | B08B 9/055 |
| 2018/0104447 A1 | 4/2018 | Madlung et al. | |
| 2018/0161539 A1 * | 6/2018 | Palmer | A61M 25/0111 |
| 2018/0369474 A1 | 12/2018 | Falleboe et al. | |
| 2019/0105462 A1 | 4/2019 | Schertiger | |
| 2019/0201659 A1 | 7/2019 | Gustavsson et al. | |
| 2020/0155261 A1 | 5/2020 | O'Flynn et al. | |
| 2020/0222659 A1 | 7/2020 | Schertiger et al. | |
| 2021/0162180 A1 | 6/2021 | Gershbaum | |
| 2021/0196923 A1 | 7/2021 | Palmer | |
| 2021/0228836 A1 | 7/2021 | Terry | |
| 2021/0260332 A1 | 8/2021 | Panesar et al. | |
| 2021/0275727 A1 | 9/2021 | Farrell et al. | |
| 2021/0290893 A1 * | 9/2021 | Palmer | A61M 27/00 |
| 2021/0290895 A1 | 9/2021 | Nielsen et al. | |
| 2021/0330929 A1 | 10/2021 | Kendrick et al. | |
| 2021/0330938 A1 | 10/2021 | Kendrick et al. | |
| 2021/0346644 A1 | 11/2021 | Kendrick et al. | |
| 2021/0346647 A1 | 11/2021 | Kendrick et al. | |
| 2021/0346648 A1 | 11/2021 | Kendrick et al. | |
| 2021/0353449 A1 | 11/2021 | Sharma et al. | |
| 2021/0370019 A1 | 12/2021 | Erbey et al. | |
| 2022/0001136 A1 | 1/2022 | Hede et al. | |
| 2022/0001139 A1 | 1/2022 | Eriksson et al. | |
| 2022/0008626 A1 | 1/2022 | Farrell et al. | |
| 2022/0023585 A1 | 1/2022 | Schertiger et al. | |
| 2022/0054295 A1 | 2/2022 | Becker | |
| 2022/0118161 A1 | 4/2022 | Bager et al. | |
| 2022/0126057 A1 | 4/2022 | Eriksson et al. | |
| 2022/0133426 A1 | 5/2022 | O'Flynn et al. | |
| 2022/0134054 A1 | 5/2022 | Schertiger et al. | |
| 2022/0176068 A1 | 6/2022 | Pfleger et al. | |
| 2022/0176069 A1 | 6/2022 | Jenco et al. | |
| 2022/0211973 A1 | 7/2022 | Palmer | |
| 2022/0226602 A1 | 7/2022 | Farrell | |
| 2022/0226604 A1 | 7/2022 | Murray et al. | |
| 2022/0233808 A1 | 7/2022 | Farrell et al. | |
| 2022/0241549 A1 | 8/2022 | Murray et al. | |
| 2022/0241553 A1 | 8/2022 | Farrell et al. | |
| 2022/0249805 A1 | 8/2022 | Pedersen | |
| 2022/0280751 A1 | 9/2022 | Farrell et al. | |
| 2022/0288350 A1 | 9/2022 | Montes de Oca et al. | |
| 2022/0347354 A1 | 11/2022 | Sileika et al. | |
| 2022/0347430 A1 | 11/2022 | Pedersen | |
| 2022/0370688 A1 | 11/2022 | Sileika et al. | |
| 2022/0370689 A1 | 11/2022 | Sileika et al. | |
| 2022/0379075 A1 | 12/2022 | Hilton et al. | |
| 2022/0387673 A1 | 12/2022 | Farrell et al. | |
| 2022/0409859 A1 | 12/2022 | Sileika et al. | |
| 2023/0241288 A1 | 8/2023 | O'Mahony et al. | |

FOREIGN PATENT DOCUMENTS

| | | | |
|---|---|---|---|
| DE | 10213411 A1 * | 10/2003 | ......... A61M 25/002 |
| EP | 3459583 A1 | 3/2019 | |
| EP | 3283136 B1 | 6/2021 | |
| EP | 3854427 A1 | 7/2021 | |
| EP | 3854438 A1 | 7/2021 | |
| EP | 3338827 B1 | 8/2021 | |
| EP | 3862031 A1 | 8/2021 | |
| EP | 3519031 B1 | 9/2021 | |
| EP | 2750749 B1 | 10/2021 | |
| EP | 3184140 B1 | 10/2021 | |
| EP | 3668555 B1 | 10/2021 | |
| EP | 3727550 B1 | 10/2021 | |
| EP | 3892320 A1 | 10/2021 | |
| EP | 3897480 A1 | 10/2021 | |
| EP | 3921009 A1 | 12/2021 | |
| EP | 3930815 A1 | 1/2022 | |
| EP | 3932438 A1 | 1/2022 | |
| EP | 3943140 A1 | 1/2022 | |
| EP | 3952973 A1 | 2/2022 | |
| EP | 3955863 A1 | 2/2022 | |
| EP | 3082929 B1 | 3/2022 | |
| EP | 3983023 A1 | 4/2022 | |
| EP | 3725355 B1 | 5/2022 | |
| EP | 3990084 A1 | 5/2022 | |
| EP | 3990085 A1 | 5/2022 | |
| EP | 3991773 A1 | 5/2022 | |
| EP | 3727549 B1 | 6/2022 | |
| EP | 4015008 A1 | 6/2022 | |
| EP | 2515988 B2 | 7/2022 | |
| EP | 2968842 B1 | 7/2022 | |
| EP | 3897766 B1 | 7/2022 | |
| EP | 4021549 A1 | 7/2022 | |
| EP | 3593850 B1 | 9/2022 | |
| EP | 3821934 B1 | 9/2022 | |
| EP | 4051328 A1 | 9/2022 | |
| EP | 4051329 A1 | 9/2022 | |
| EP | 4051330 A1 | 9/2022 | |
| EP | 4051358 A1 | 9/2022 | |
| EP | 4061463 A1 | 9/2022 | |
| EP | 3257546 B1 | 10/2022 | |
| EP | 4085962 A1 | 11/2022 | |
| EP | 4088749 A1 | 11/2022 | |
| EP | 2688629 B1 | 12/2022 | |
| EP | 3308823 B1 | 12/2022 | |
| EP | 3793626 B1 | 12/2022 | |
| EP | 4101492 A1 | 12/2022 | |
| EP | 2908898 B1 | 7/2023 | |
| EP | 3148625 B1 | 7/2023 | |

(56) References Cited

FOREIGN PATENT DOCUMENTS

| | | | |
|---|---|---|---|
| EP | 3651844 | B1 | 7/2023 |
| EP | 3119464 | B2 | 8/2023 |
| EP | 3921009 | B1 | 8/2023 |
| EP | 3990085 | B1 | 8/2023 |
| EP | 3421071 | B1 | 9/2023 |
| EP | 3883630 | B1 | 9/2023 |
| EP | 4241818 | A2 | 9/2023 |
| EP | 4245349 | A2 | 9/2023 |
| EP | 3040097 | B2 | 10/2023 |
| EP | 3299056 | B2 | 10/2023 |
| EP | 3041560 | B1 | 11/2023 |
| EP | 3419681 | B1 | 11/2023 |
| EP | 3721910 | B1 | 11/2023 |
| EP | 4138970 | B1 | 11/2023 |
| EP | 4138972 | B1 | 11/2023 |
| EP | 4268859 | A2 | 11/2023 |
| GB | 2540125 | B | 1/2017 |
| GB | 2596593 | A | 1/2022 |
| WO | 2019014344 | A1 | 1/2019 |
| WO | 2019123003 | A1 | 6/2019 |
| WO | 2021183718 | A1 | 9/2021 |
| WO | 2021219188 | A1 | 11/2021 |
| WO | 2021228341 | A1 | 11/2021 |
| WO | 2021231724 | A1 | 11/2021 |
| WO | 2021240266 | A1 | 12/2021 |
| WO | 2021242487 | A1 | 12/2021 |
| WO | 2021242676 | A1 | 12/2021 |
| WO | 2021242745 | A1 | 12/2021 |
| WO | 2022002483 | A1 | 1/2022 |
| WO | 2022003619 | A1 | 1/2022 |
| WO | 2022031550 | A1 | 2/2022 |
| WO | 2022090055 | A1 | 5/2022 |
| WO | 2022108750 | A1 | 5/2022 |
| WO | 2022118010 | A1 | 6/2022 |
| WO | 2022118011 | A1 | 6/2022 |

OTHER PUBLICATIONS

Written Opinion of the International Searching Authority; European Patent Office; International Application No. PCT/GB2021/050983; Aug. 10, 2021; 5 pages.

* cited by examiner

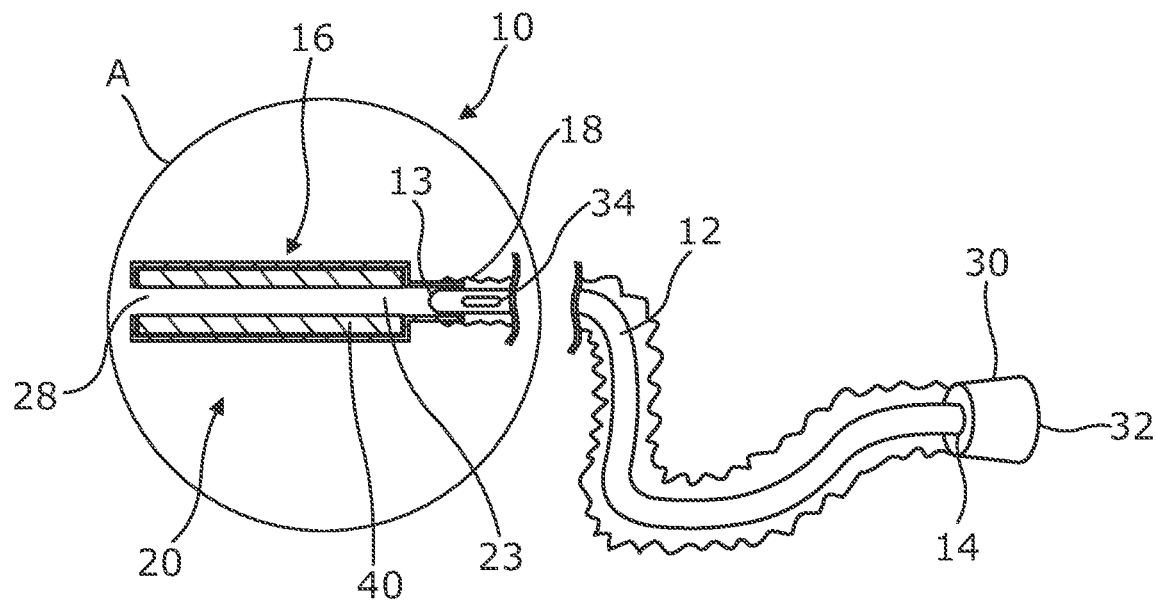
Fig. 1A
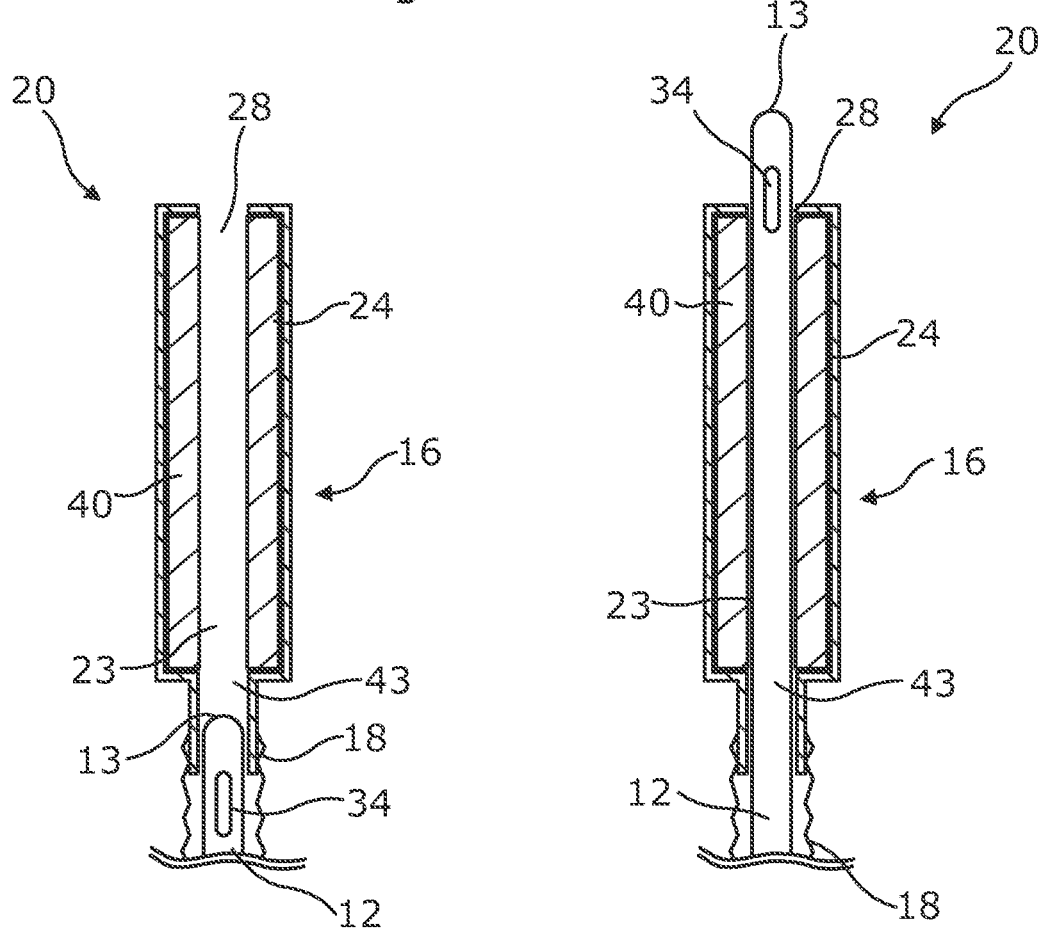
Fig. 1B
Fig. 1C

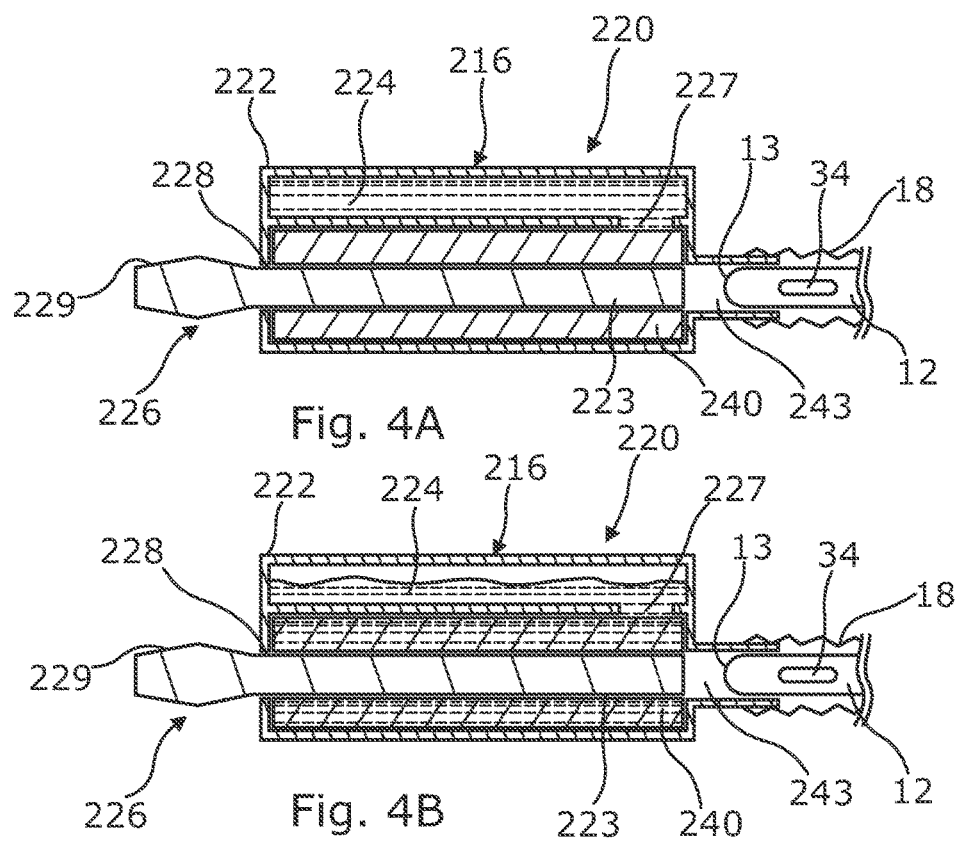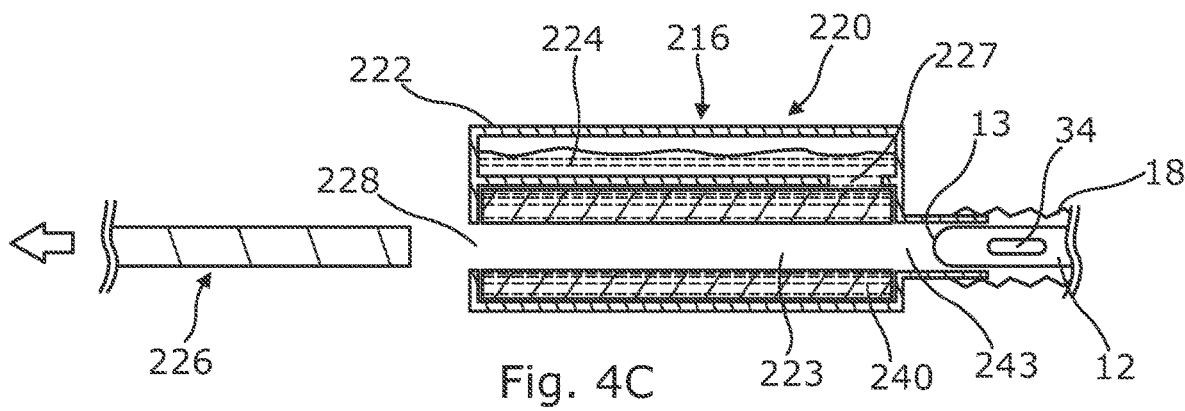

WETTING MECHANISM FOR A CATHETER

TECHNICAL FIELD OF THE INVENTION

The present invention relates to a wetting mechanism for a catheter (e.g. a urinary catheter) for wetting a tube of the catheter, in use. The invention extends to a catheter comprising the wetting mechanism and a method for wetting a catheter tube.

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

To maximise comfort and minimise the risk of trauma and/or infection, an outer surface of the catheter tube is typically wetted using a wetting fluid prior to insertion by the user. In further developments, the catheter tube itself comprises, is integrated with or is coated with a hydrophilic component (e.g. a hydrophilic polymer) which serves to reduce friction further upon application of the wetting fluid.

Some catheters may be supplied pre-wetted in a packaging, for instance, where the catheter is at least partially submerged within wetting fluid within the packaging. Whilst this may ensure the catheter tube is adequately wetted prior to use, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be wetted at or immediately prior to the point of use.

In an attempt to address this, some catheters are provided in packaging which includes a rupturable container or sachet within the packaging which a user may burst to release the wetting fluid. Typically, this involves the user squeezing the packaging to cause the container/sachet to break. However, such arrangements experience similar problems to those discussed above where the wetting fluid is allowed to come into contact with other components of the catheter. Such arrangements also result in the possibility of the catheter tube not being fully wetted, or indeed wetted at all, prior to use. This can be harmful for the user.

It is therefore advantageous to provide a catheter which includes a means of supplying a wetting fluid solely to the catheter tube to improve user experience.

In further prior art solutions, the catheter may be packaged within a packaging which includes a wetting device. In use, the catheter tube may be moved through the wetting device as the catheter is removed from the packaging and in doing so wetting the catheter tube. Examples of such catheters are shown in PCT application No. PCT/IB2018/001539 in the name of Convatec Limited.

However, due to packaging constraints the amount of wetting fluid able to be contained in such wetting devices is low, and there therefore remains a possibility of the catheter tube not being fully wetted in such solutions, especially where the catheter is a male urinary catheter which might be up to and possibly in excess of 35 cm in length.

For mechanisms which wet the catheter tube from the distal end, an insufficient volume of wetting fluid may result in the tip end not being wetted at all which is undesirable since the tip end will be introduced into the urethra first and is hence most likely to cause injury if inadequately wetted before use. Further, if using an arrangement wherein the catheter tube is wetted by pulling the tube from its distal end through a wetting device, thereby exposing the length of the catheter tube, a male user may then find it extremely difficult if not impossible to correctly manoeuvre and position a long, flexible catheter tube without touching the tube itself, thereby risking contamination.

If using an arrangement wherein the catheter tube is pushed out of a packaging and thereby through a wetting device (e.g. using the plunger arrangement shown in FIGS. 23-26 of PCT/IB2018/001539) the length and flexibility of the male catheter tube would make this action difficult if not impossible for the user as the tube may simply bend along its length rather than being pushed through the wetting device. Further, the packaging itself would have to be of considerable size e.g. potentially twice the 30-40 cm length of a typical male catheter tube to accommodate both the male catheter tube and a plunger, which would need to be of a length broadly equal to the catheter tube. Accordingly, mechanisms of this type are generally only suited for use with female catheters where the length of the catheter tube is much shorter and which are, accordingly, stiffer and easier to manoeuvre and insert whilst holding only the distal end (opposite the tip of the catheter).

It would therefore be advantageous to provide a system which mitigates the possibility of a male catheter tube being used prior to or without adequate lubrication.

It is an aim of an embodiment or embodiments of the invention to overcome or at least partially mitigate one or more problems with the prior art.

SUMMARY OF THE INVENTION

According to an aspect of the invention there is provided a wetting mechanism for wetting a tube of a catheter, the wetting mechanism comprising: a housing configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and wherein the wetting mechanism comprises a wetting applicator positioned within the wetting chamber configured to control release of fluid onto the catheter tube to wet the catheter tube, in use.

According to an aspect of the invention there is provided a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and wherein the wetting mechanism comprises a wetting applicator positioned within the wetting chamber configured to hold fluid therein and release said fluid to wet the catheter tube upon movement of the tube through the wetting chamber.

Advantageously, the wetting mechanism of the present invention provides a wetting applicator at or proximal to the tip end of the catheter tube. This ensures the catheter tube is wetted from the tip end (i.e. the end that will be introduced into the urethra first, in use) and thereby reduces the likelihood of injury for the user due to inadequate wetting of the catheter tube. Furthermore, the wetting applicator is advantageously used to control the amount of fluid applied across the catheter tube surface, with the aim of obtaining a substantially even coating of wetting fluid. Having the wetting mechanism at or proximal to the tip end, and requiring the catheter tube to moved therethrough prior to use may advantageously wet the catheter tube irrespective of the orientation of the catheter and wetting mechanism. In this way, the user can be confident that the tube will be adequately wetted at any angle.

The housing may advantageously form a separate and moveable (e.g. with respect to the catheter tube and/or other components of the catheter—e.g. a funnel) component of the catheter which acts as a gripping element in both handling the catheter whilst wetting the catheter tube, and handing the catheter whilst positioning and subsequently inserting the catheter tube into the urethra, in use. Having the wetting mechanism configured as part of a gripping element for the catheter improves the usability of the catheter in terms of both the wetting action and ultimately the use of the catheter. For instance, the gripping element may be moved relative to the catheter tube—i.e. along the tube to move the tube through the wetting chamber (thereby wetting the tube and exposing the tip end of the catheter tube), rather than in the prior art solutions where the catheter tube may need to be pushed or pulled through a wetting device, thereby mitigating problems caused by the length of the catheter tube of a male catheter. Furthermore, the gripping element can be used to hold the catheter tube close to the urethra to help a user guide the catheter tube without having to touch the tube itself, thereby mitigating potential contamination issues.

Optional features set out below may apply to any aspect of the invention as appropriate.

The housing may comprise a holding chamber. The holding chamber may contain a volume of wetting fluid therein. The wetting chamber may be fluidly connected or connectable to the holding chamber. Having the wetting chamber fluidly connected (or at least connectable) to a holding chamber containing the wetting fluid ensures the wetting applicator can be automatically/readily "topped up" with fluid from the holding chamber, for example, as the fluid held within the wetting applicator is released onto the catheter tube, in use. This may ensure there is sufficient fluid to coat the entire length of the catheter tube, which may up to and possibly greater than 35 cm where the catheter is a male urinary catheter.

The wetting applicator may comprise a flexible, compressible and/or resilient material. The wetting applicator may be deformable under the application of a force thereto, for example, upon movement of the catheter tube through the wetting chamber. Deformation of the wetting applicator may cause release of fluid held therein. Accordingly, movement of the catheter tube through the wetting chamber, e.g. in contact with and deforming the wetting applicator may automatically release fluid from the wetting applicator onto a surface of the catheter tube, in use.

The wetting applicator may comprise an absorbent material. For example, in some embodiments the wetting applicator comprises a sponge or foam material, operable to absorb the fluid, in use. In embodiments wherein the housing comprises a holding chamber, the absorbent material may be provided between the holding chamber and the wetting chamber, or may at least partly define the wetting chamber, for example, and be operable to absorb fluid from the holding chamber for subsequent application to the catheter tube as the catheter tube is moved through the wetting chamber, in use.

The wetting applicator may comprise a plastics material, such as polyethylene or polyurethane, for example. The foam or sponge material may comprise an open cell material, which may comprise an open cell hydrophilic foam material, for example. The foam or sponge material may be non-swelling, or at least substantially non-swelling, when exposed to the fluid. Advantageously, the dimensions of a non-swelling material may remain roughly constant during use, which may be particularly advantageous for use within a housing of the wetting mechanism of the invention.

The wetting applicator may comprise a wicking material. The wicking material may be operable in use to draw the fluid therethrough for application to the catheter tube. In embodiments wherein the housing comprises a holding chamber, the wicking material may be provided between the holding chamber and the wetting chamber, or may at least partly define the wetting chamber, for example, and be operable to draw fluid from the holding chamber for application to the catheter tube as the catheter tube is moved through the wetting chamber, in use. The wicking material may comprise polyester or nylon, for example.

The wetting applicator may comprise a baffle arrangement. The baffle arrangement may define a plurality of subregions of the wetting applicator each configured to hold a portion of the fluid held within the wetting applicator. For example, the baffle arrangement may define a plurality of subregions within the housing, e.g. within the wetting chamber of the housing in which the fluid may reside and or be released into. The baffle arrangement may at least partially define a holding chamber of the housing.

One particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and herein the wetting mechanism comprises a wetting applicator positioned within the wetting chamber configured to hold fluid therein and release said fluid to wet the catheter tube upon movement of the tube through the wetting chamber; wherein the wetting applicator comprises a baffle arrangement.

Another particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and herein the wetting mechanism comprises a wetting applicator positioned within the wetting chamber configured to hold fluid therein and release said fluid to wet the catheter tube upon movement of the tube through the wetting chamber; wherein the wetting applicator comprises a baffle arrangement which defines a plurality of subregions of the wetting applicator each configured to hold a portion of the fluid held within the wetting applicator.

Another particularly preferred embodiment provides a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and herein the wetting mechanism comprises a wetting applicator positioned within the wetting chamber configured to hold fluid therein and release said fluid to wet the catheter tube upon movement of the tube through the wetting chamber; wherein the wetting applicator comprises a baffle arrangement which defines a plurality of subregions within the wetting chamber in which the fluid may reside and/or be released into.

The wetting applicator may comprise a volume of aggregate material through which the wetting fluid may flow before wetting the catheter tube. The aggregate material may advantageously control the flow of the wetting fluid, e.g. between a holding chamber and a wetting chamber of the housing. The aggregate material may comprise a particulate material, for example. The aggregate material is non-soluble.

The wetting applicator may define a channel within the wetting chamber. The wetting applicator may at least partially define the wetting chamber of the wetting mechanism. The wetting applicator may define a channel within the wetting chamber through which the catheter tube is able to be moved through, in use. The wetting mechanism may be configured such that the catheter tube is moved in contact with the wetting applicator as it is moved through the wetting chamber (e.g. along the channel defined by the wetting applicator). In embodiments, the wetting applicator may be configured such that fluid held within the wetting applicator is able to be released, and preferably is automatically released, therefrom upon movement of the catheter tube through the wetting chamber.

The tip end of the catheter tube may, at least initially, be disposed outside the wetting chamber. The tip end of the catheter tube may, at least initially, be held within an inlet of the wetting chamber.

The wetting mechanism may comprise a fluid release control component.

The fluid release control component may be operable, in use, to control release of the fluid from the wetting applicator. For example, the fluid release control component may, in a first configuration, act to prevent the catheter tube from being brought into proximity and/or contact with the wetting applicator. The fluid release control component may act as a barrier between the wetting applicator and a channel through the wetting chamber through which the catheter tube may be moved, in use.

Additionally or alternatively, the fluid release control component may be operable, in use, to control release of the fluid from the holding chamber into the wetting chamber. The fluid release control component may be operable to control release of the fluid from the holding chamber onto and/or into the wetting applicator. In other words, the wetting mechanism may comprise a fluid release control component operable to fluidly connect the holding chamber and the wetting chamber, in use.

Advantageously, controlling the release of the fluid from a holding chamber where it is held out of contact with other components of the catheter system overcomes issues with some prior art devices, particularly where catheters may be disadvantageously submerged in wetting fluid prior to use. It may also improve the shelf life of the catheter by reducing the exposure of most of the components of the catheter to moisture until (or as close as possible to) the point of use.

The fluid release control component may comprise a moveable plug. The plug may be moveable between first and second positions. In the position, the fluid release control component may prevent release of the fluid from the holding chamber to the wetting chamber and/or the wetting applicator. In the second position, the fluid release control component may allow release of the fluid from the holding chamber to the wetting chamber and/or the wetting applicator. The plug may be linearly moveable between first and second positions. For example, in use, the plug may be pushed or pulled by a user to move the plug between the first and second positions. Alternatively, the plug may be may be rotatable between first and second angular positions. The first and second angular positions may correspond to the first and second positions of the plug. The plug may be threaded, and may be provided within the wetting mechanism through interaction with a complementary threaded surface of the wetting mechanism, for example a complementary threaded surface provided on or within the wetting chamber of the housing.

The plug may be configured to be at least partly withdrawn from the wetting mechanism. The plug may be configured to be at least partly withdrawn from the wetting chamber of the wetting mechanism. Partial withdrawal of the plug may correspond to movement of the plug from the first position to the second position. The plug may be configured to be only partly withdrawn from the wetting mechanism—i.e. it cannot be fully withdrawn from the wetting mechanism. It may remain attached or otherwise coupled to the housing whether in the first or second position. In embodiments, the plug may be configured to be fully withdrawn from the wetting mechanism (optionally from the wetting chamber of the wetting mechanism).

Movement of the plug between first and second positions may expose or otherwise unblock one or more openings within the housing between the holding chamber and the wetting chamber. Accordingly, fluid at least initially contained within the holding chamber may be released from said holding chamber (and into the wetting chamber/onto or into the wetting applicator) upon movement of the plug between first and second positions.

The fluid release control component may comprise a container, such as a sachet, blister pack or capsule, for example. The container may be positioned within the holding chamber, or may at least partially define the holding chamber of the wetting mechanism, and may have the fluid contained therein. The container may be rupturable or otherwise openable to release fluid contained therein.

The wetting mechanism may be configured such that the container may be ruptured or otherwise opened, in use, through user action on the housing itself. For example, in some embodiments the housing is formed at least partly from a flexible, compressible and/or resilient material. In such embodiments, the wetting mechanism may be configured such that the container may be ruptured or otherwise opened upon a user compressing, bending and/or flexing the housing.

In further embodiments, the wetting mechanism may comprise a fluid release control component in the form of a plug, in combination with the container. In such embodiments, the wetting mechanism may be configured such that the container may be ruptured or otherwise opened, in use, through movement of the plug. For example, the wetting mechanism may be configured such that the container is compressed upon (at least partial) withdrawal of the plug, or upon rotation of the plug.

The wetting chamber may comprise an inlet through which the catheter tube is able to be introduced into the wetting chamber. The wetting mechanism may comprise a moveable or removeable stopper configured to block, or at least partially block the inlet. In some embodiments the wetting mechanism may be configured such that movement of the stopper (e.g. movement of the stopper from a first position to a second position, or indeed removal of the stopper) unblocks the inlet, thereby allowing for the catheter tube to be introduced into the wetting chamber (and be moved therethrough). In embodiments, the stopper may comprise or be combined with the fluid release control component, e.g. the plug. For example, in such embodiments, at least part withdrawal of the plug may cause both release of the wetting fluid and unblocking of the inlet of the wetting chamber.

The wetting chamber may have an outlet through which the catheter tube may be moved to expose the catheter tube for subsequent insertion by the user.

The inlet and/or outlet may be sealed. For example, the inlet and/or outlet may comprise a valve. The or each valve may provide a seal to retain the wetting fluid within the housing. The valve(s) may advantageously prevent the wetting fluid from being expelled unintentionally from the housing and, for example, onto a user.

The valve(s) may be configured to allow the catheter tube to be moved therethrough. For example, where the housing comprises a valve at the inlet, the inlet valve may be configured to allow the catheter tube to be moved therethrough to introduce the catheter tube into the wetting chamber of the housing. Where the housing comprises a valve at the outlet, the outlet valve may be configured to allow the catheter tube to be moved therethrough to expose the catheter tube, e.g. for subsequent use/insertion by the user.

The housing—e.g. the wetting chamber and/or the holding chamber—may be configured to hold up to 0.25 ml, or up to 0.5 ml, or up to 0.75 ml, or up to 1.0 ml, or up to 1.5 ml, or up to 2.0 ml, or up to 2.5 ml, or up to 3.0 ml, or up to 4.0 ml, or up to 5.0 ml, or up to 7.5 ml, or up to 10 ml of wetting fluid, for example.

The housing forms a gripping element of the catheter. As described herein, in use, a gripping element may be used by a user to control application of the catheter. For example, the gripping element can be used to hold the catheter tube close to the urethra to help a user guide the catheter tube without having to touch the tube itself. In embodiments, the housing may comprise a conical profile, which may assist with the user gripping and acting on the housing, in use.

In embodiments wherein the wetting mechanism comprises a fluid release control component in the form of a plug, the plug may comprise a conical profile. The plug may comprise a hollow or substantially hollow interior. Where combined with a conical profile, such a plug may form a cup shape element which may assist a user with locating the catheter tube, in use. The cup can, for example, be used to locate the housing over the tip of a penis such that the catheter tube can be easily inserted into the urethra immediately after wetting.

In some embodiments, the housing and the plug both comprise a conical profile. In such embodiments, the wetting mechanism may be configured such that, together, the housing and the plug form a substantially hourglass-shaped profile. An hourglass-shaped profile may be particularly advantageous in that it may allow the user to operate the wetting mechanism—i.e. to remove (or at least partially remove) the plug from the housing using only one hand.

According to an aspect of the invention there is provided a wetting mechanism for wetting a tube of a catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and wherein the wetting mechanism is configured such that the catheter tube is wetted upon movement of the tube through the wetting chamber.

According to an aspect of the invention there is provided a wetting mechanism for wetting a tube of a male urinary catheter, the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and wherein the wetting mechanism is configured such that the catheter tube is wetted with wetting fluid contained within the housing upon movement of the tube through the wetting chamber.

Advantageously, the wetting mechanism is configured such that the catheter tube is wetted from the tip end (i.e. the end that will be introduced into the urethra first, in use) and immediately prior to insertion by the user. This thereby reduces the likelihood of injury for the user due to inadequate wetting of the catheter tube, e.g. due to a lack of wetting fluid or drying of the catheter tube due to a delay between the wetting process and subsequent insertion by the user.

As mentioned above, the optional aspects of the invention described above may apply to any aspect of the invention—for avoidance of doubt, where compatible, that includes the aspects of the invention mentioned immediately above.

The wetting fluid may be contained within the wetting chamber. The wetting fluid may be contained within a holding chamber within the housing. The holding chamber and wetting chamber may be fluidly connected, e.g. to allow for wetting fluid to enter the wetting chamber for wetting the catheter tube as it is moved therethrough. For example, the housing may comprise an opening or a port located between the holding chamber and the wetting chamber, and through which the wetting fluid may flow. The opening or port may be configured such that the rate at which the wetting fluid may flow therethrough is limited by the surface tension of the wetting fluid. In this way, the flow of wetting fluid into the wetting chamber may be advantageously controlled to control the application of wetting fluid onto the catheter tube, in use.

The housing may have an inlet and an outlet. The inlet and/or outlet may be sealed. For example, the inlet and/or outlet may comprise a valve. The or each valve may provide a seal to retain the wetting fluid within the housing. The valve(s) may advantageously prevent the wetting fluid from being expelled unintentionally from the housing and, for example, onto a user.

The valve(s) may be configured to allow the catheter tube to be moved therethrough. For example, where the housing comprises a valve at the inlet, the inlet valve may be configured to allow the catheter tube to be moved therethrough to introduce the catheter tube into the wetting chamber of the housing. Where the housing comprises a valve at the outlet, the outlet valve may be configured to allow the catheter tube to be moved therethrough to expose the catheter tube, e.g. for subsequent use/insertion by the user.

According to an aspect of the invention there is provided a wetting mechanism for wetting a tube of a catheter, the wetting mechanism comprising: a housing forming a gripping element for the catheter, the housing being configured to be positioned initially at or proximal to the tip end of the catheter tube; wherein the housing comprises: a holding chamber for containing a volume of fluid therein; and a wetting chamber fluidly connected or connectable to the holding chamber and configured such that at least a portion of the catheter tube is able to be introduced and be moved therethrough to move at least a portion of the catheter tube through the wetting chamber, in use; and wherein the wetting mechanism comprises a wetting applicator positioned within the wetting chamber configured to hold fluid therein and release said fluid to wet the catheter tube upon movement of the tube through the wetting chamber.

According to an aspect of the invention there is provided a catheter, comprising: a catheter tube having a tip end and a distal end; and the wetting mechanism of any preceding aspect operably coupled at or proximal to the tip end of the catheter tube for wetting the catheter tube, in use.

According to an aspect of the invention there is provided a male urinary catheter, comprising: a catheter tube having a tip end and a distal end; and the wetting mechanism of any preceding aspect operably coupled at or proximal to the tip end of the catheter tube for wetting the catheter tube, in use.

The catheter may comprise a funnel. The funnel may be provided at or proximal to the distal end of the catheter tube. The funnel may comprise a fluid outlet for the discharge of fluid from within the catheter tube. Preferably the catheter comprises the wetting mechanism at or proximal to the tip end of the catheter tube, with the funnel at or proximal to the distal end of the catheter tube, with the wetting mechanism and funnel being separate components coupled via the catheter tube.

In embodiments, the catheter comprises a sleeve. The sleeve may be positioned about the catheter tube. In embodiments, the sleeve may define an internal volume about at least a portion of the catheter tube. The sleeve may comprise a flexible material. The sleeve may be thin and readily crumpled. For example, the sleeve may be formed of a film of plastics material, which may be low-density polyethylene, for example.

The sleeve may be coupled to the wetting mechanism. For example, the sleeve may be coupled at a first end to the wetting mechanism. In such embodiments, the sleeve may be coupled to the catheter at a second, opposing end; for example, it may be coupled to a funnel at or proximal to a distal end of the catheter tube. In this way, the sleeve may define an internal volume about the catheter tube between the wetting mechanism at or proximal to the tip end of the catheter tube, and a funnel at or proximal to a distal end of the catheter tube.

One particularly preferred embodiment provides a male urinary catheter, comprising: a catheter tube having a tip end and a distal end; and a wetting mechanism operably coupled at or proximal to the tip end of the catheter tube for wetting the catheter tube, in use; the wetting mechanism comprising: a housing forming a gripping element for the catheter, the housing being configured to be positioned initially at or proximal to the tip end of the catheter tube; wherein the housing comprises a wetting chamber into which at least a portion of the catheter tube is able to be introduced and be moved therethrough to move at least a portion of the catheter tube through the wetting chamber, in use; and wherein the wetting mechanism comprises a wetting applicator positioned within the wetting chamber configured to hold fluid therein and release said fluid to wet the catheter tube upon movement of the tube through the wetting chamber; the catheter further comprising a funnel provided at or proximal to the distal end of the catheter tube, with the wetting mechanism and funnel being separate components coupled via the catheter tube; and the catheter comprising a sleeve formed of a film of plastics material positioned about the catheter tube, defining an internal volume about at least a portion of the catheter tube; the sleeve being coupled at a first end to the wetting mechanism and at a second, opposing end to the funnel.

The sleeve may advantageously form an interaction point for a user of the catheter. For example, in use, the user may grip the catheter at both the housing of the wetting mechanism and at a point along the sleeve. The catheter may be configured such that the user may then, through indirect contact with the tube via the sleeve, act to urge the catheter tube in and through the wetting chamber of the wetting mechanism. In this way, the catheter of the invention may be used to assist in the wetting of the catheter tube (and exposure of the tip end of the tube for subsequent insertion into the urethra) without a user having to contact the catheter tube directly. Advantageously, this may reduce the risk of contamination.

The catheter may be configured such that at least a portion of the fluid within the wetting chamber of the wetting mechanism is able to flow into and along the sleeve to wet the catheter tube, in use. For example, in some embodiments the housing of the wetting mechanism comprises an aperture or opening therein allowing fluid within the wetting chamber to flow into the sleeve.

The catheter may comprise a single-use catheter. The catheter may comprise an intermittent urinary catheter.

The catheter tube may have a length of up to (and possibly upwards) of 35 cm.

The catheter tube may be up to or at least 20 cm, up to or at least 25 cm, up to or at least 30 cm, up to or at least 35 cm, or up to or at least 40 cm, in length, for example. In embodiments, the catheter tube may be more than 40 cm in length. In preferred embodiments, the catheter tube is between 25-35 cm, in length. Male catheters typically have a catheter tube of such lengths and are therefore less suited to mechanisms which wet the catheter tube from the distal end (as opposed to the tip end as in the present invention), as the fluid may not adequately cover the entire length of the tube. This potentially results in the tip end being wetted last (or not at all if there is insufficient fluid), which is undesirable since the tip end will be introduced into the urethra first and is hence most likely to cause injury if inadequately wetted before use. Further, due to the length requirements of male catheters, wetting arrangements whereby the catheter tube is wetted by a wetting device integrated within the catheter packaging are generally also unsuitable.

The catheter tube may comprise, may be integrated with, or may be coated with a hydrophilic component. The hydrophilic component may be configured to provide a low friction surface (e.g. outer surface) of the catheter tube upon application of the wetting fluid. The hydrophilic component may comprise a hydrophilic polymer, for example.

According to an aspect of the invention there is provided a sealed packaged catheter according to the preceding aspect of the invention, wherein the wetting mechanism is operably coupled at or proximal to the tip end of the catheter tube within the sealed package.

According to an aspect of the invention there is provided a method for wetting a tube of a catheter using the wetting mechanism of any aspect described herein, the method comprising: introducing the tip end of the catheter tube into the wetting chamber and moving it therethrough, causing release of the fluid from the wetting applicator thereby wetting the at least a portion of an outer surface of the catheter tube.

The method may comprise operating a fluid release control component to control release of fluid from the holding chamber into the wetting chamber, and preferably from the holding chamber onto or into the wetting applicator positioned within (or at least partly defining) the wetting chamber.

DETAILED DESCRIPTION OF THE INVENTION

In order that the invention may be more clearly understood one or more embodiments thereof will now be described, by way of example only, with reference to the accompanying drawings, of which:

FIG. 1A is a schematic overview of a first embodiment of the invention;

FIGS. 1B-1C are a series of cross-sectional schematic views of section A in FIG. 1A illustrating the operational use of the illustrated device;

FIGS. 4A-4D are a series of cross-sectional schematic views illustrating the operational use of a fourth embodiment of the invention;

Figure 2A:
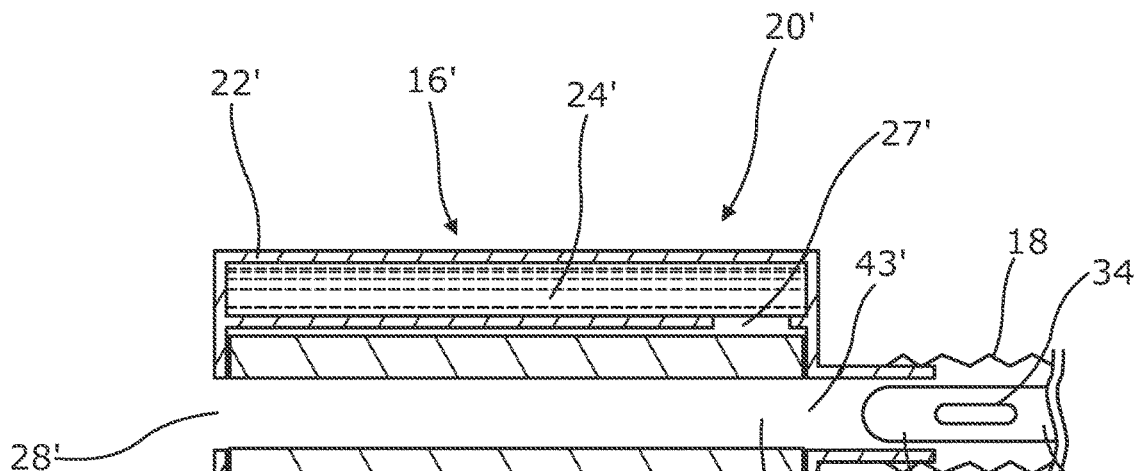
FIGS. 2A-2C are a series of cross-sectional schematic views illustrating the operational use of a second embodiment of the invention.

In general, the present invention relates to a catheter 10, 410, and specifically to a wetting mechanism 20, 20', 120, 220, 320, 420 configured for use to wet a tube 12, 412 of the catheter 10, 410, in use.

The Figures illustrate a series of embodiments of the invention. Where equivalent components are present between embodiments, like reference numerals have been used.

FIGS. 1A-1C illustrate a first embodiment of a wetting mechanism 20 for use in wetting a tube 12 of a catheter 10.

The catheter 10 includes the catheter tube 12, with the wetting mechanism 20 provided at a tip end (proximal end) 13 of the catheter tube 12 and a funnel 30 at a distal end 14 of the catheter tube 12. A sleeve 18 is provided between the wetting mechanism 20 and the funnel 30, enclosing the catheter tube 12 therebetween. Here, the sleeve 18 is formed of a flexible material and is coupled at a first end to a housing 16 of the wetting mechanism 20 and at a second end to the funnel 30. In this way, the sleeve 18 defines an internal volume about the catheter tube 12 into which, in some instances, fluid may be introduced to wet the outer surface of the catheter tube 12.

As mentioned above, the catheter tube 12 has a tip end 13 and a distal end 14. The tip end 13 includes a tip for insertion of the catheter tube 12 into a canal, vessel, passageway, body cavity, etc. for removal of fluid therefrom. Here, the catheter 10 comprises a male urinary catheter 10 with the tip configured for insertion into a male patient's bladder. The tip end 13 of the catheter tube includes an aperture 34 therein for allowing for fluid to enter the interior of the catheter tube 12. The distal end 14 of the catheter tube 12 is provided within the funnel 30. Specifically, the distal end 14 of the catheter tube 12 is located within the funnel 30 and opens into the funnel 30, which defines a fluid outlet 32 serving as an outlet for discharging fluid from within the catheter tube 12. The catheter tube 12 itself comprises a hydrophilic coating which acts to provide a low friction outer surface of the catheter tube 12 upon application of a wetting fluid 24.

The wetting mechanism 20 includes a tubular housing 16 positioned (at least initially) at a tip end 13 of the catheter tube 12. The housing includes an inlet 43 and outlet 28 through which the catheter tube 12 may be moved, in use. Specifically, the catheter tube 12 may be introduced into the housing 16 through the inlet 43, and may be moved out of the housing 16 through the outlet 28 to expose the tip end 13 thereof, i.e. for subsequent insertion into the urethra.

A wetting applicator in the form of a foam conduit 40 is provided within the wetting chamber 23, and is configured to hold wetting fluid 24 therein and to control application of the fluid to the catheter tube 12, in use, as the catheter tube 12 is moved through the wetting chamber 23. The wetting chamber 23, and specifically the foam conduit 40 define a channel through the housing 16 through which at least a portion of the catheter tube 12 is able to be introduced and be moved therethrough. The channel is defined between the inlet 43 and outlet 28 of the housing 16 such that the catheter tube 12 is moved along the length of the foam conduit 40 in moving through the housing 16. When moving through the channel, the catheter tube 12 is brought into contact with the foam conduit 40 resulting in a force being applied to the foam conduit 40 causing it to compress. The compression of the foam conduit 40 causes fluid stored therein to be released directly on to the outer surface of the catheter tube 12, thereby providing a coating of fluid 24 on the catheter tube 12 as it is moved through the wetting chamber 23.

Once the tip end 13 of the catheter tube 12 is moved out through the outlet 28 of the housing 16, the tip end 13 then becomes exposed for insertion by the user. The housing 16 then acts as a gripping element for the user to direct the catheter tube 12, in use, as the user may then use the housing 16 to easily direct the exposed tip end 13 of the catheter tube 12 without contacting the tube 12 directly.

A wetting applicator of this type may advantageously ensure that the wetting fluid 24 is applied substantially evenly across the outer surface of the catheter tube 12, and reduce the prospect of any spillage. Further, having the wetting mechanism 20 provided as a gripping element for the catheter 10 improves the usability of the catheter 10 in terms of both the wetting action and ultimately the use of the catheter.

Figure 2B:
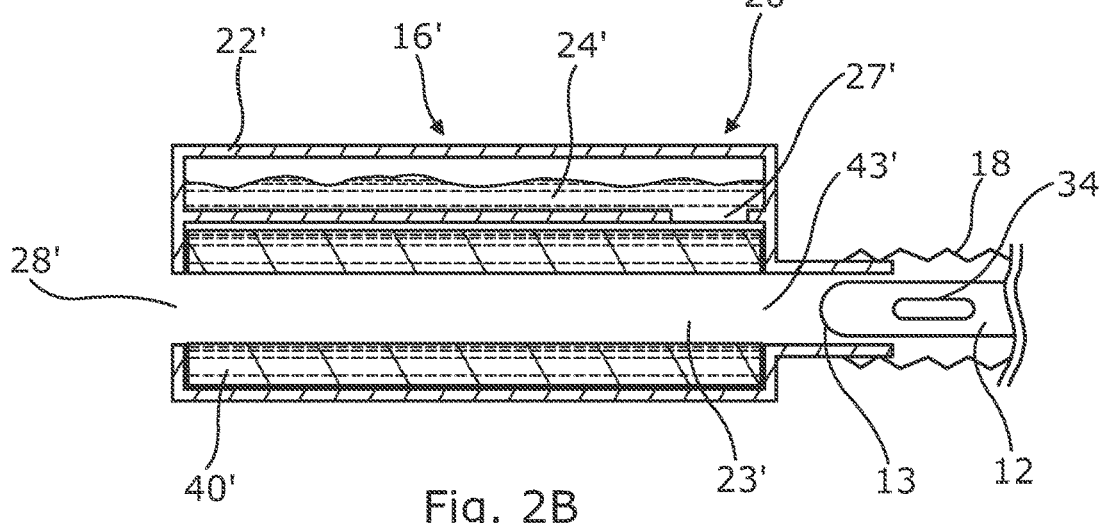
Figure 2C:
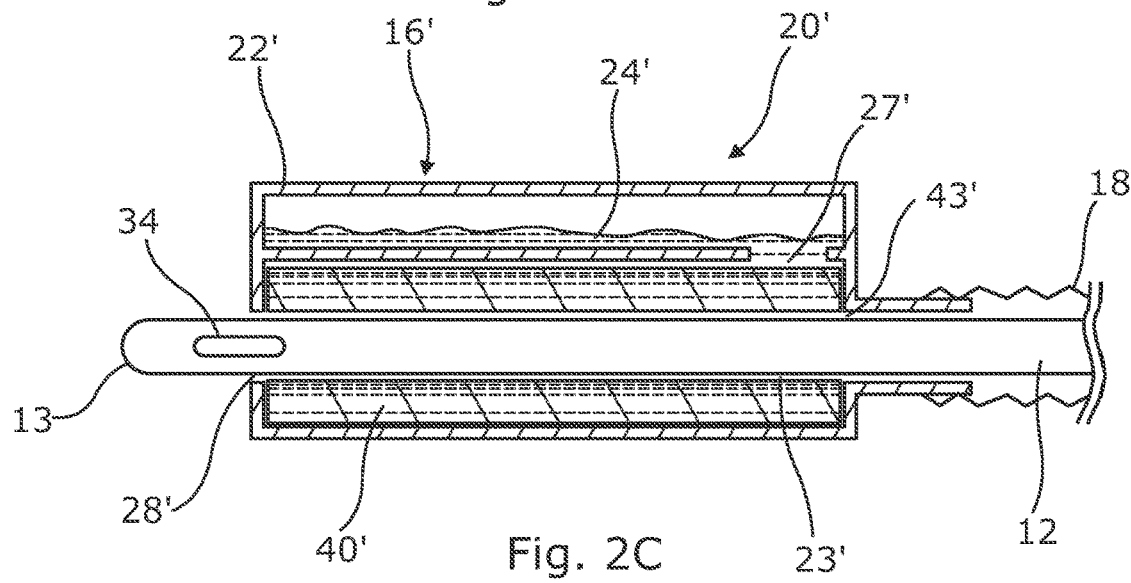

A variant of wetting mechanism 20 is shown in FIGS. 2A-2C. Specifically, these figures shown a wetting mechanism 20' configured similarly to wetting mechanism 20. Wetting mechanism 20' differs in that it comprises a housing 16' which further includes a holding chamber 22' which contains a volume of fluid 24 therein for wetting the catheter tube 12. In use, the fluid 24' may be released from said holding chamber 22' into the wetting chamber 23', and specifically onto a wetting applicator in the form of a foam conduit 40' positioned within the wetting chamber 23'. The fluid 24' is released from the holding chamber 22' to the wetting chamber 23' through an opening 27' within the housing 16'.

As with foam conduit 40, the foam conduit 40' is configured to hold fluid, but specifically here fluid 24' released into the wetting chamber 23' from the holding chamber 22'. Again, foam conduit 40' is configured to control application of the fluid to the catheter tube 12, in use, as the catheter tube 12 is moved through the wetting chamber 23'.

The catheter tube 12 may be moved into and through the wetting chamber 23' via the inlet 43' in the same manner as wetting mechanism 20 described above, bringing the catheter tube 12 into contact with (and apply pressure to) the foam conduit 40'. This pressure causes release of the fluid 24' from the foam conduit 40', thereby wetting an outer surface of the catheter tube 12. Once the tip end 13 of the catheter tube 12 is moved out through an outlet 28' of the housing 16', the tip end 13 then becomes exposed for insertion by the user. The housing 16' then acts as a gripping element for the user to direct the catheter tube 12, in use, as the user may then use the housing 16' to easily direct the exposed tip end 13 of the catheter tube 12 without contacting the tube 12 directly.

A wetting applicator of this type may advantageously ensure that the foam conduit 40' can be "topped up" with fluid 24' from the holding chamber 22' as the fluid held within the foam conduit 40' is released onto the catheter tube 12. This may ensure there is sufficient fluid to coat the entire length of the catheter tube 12, which may up to and possibly greater than 35 cm.

Figure 3A:
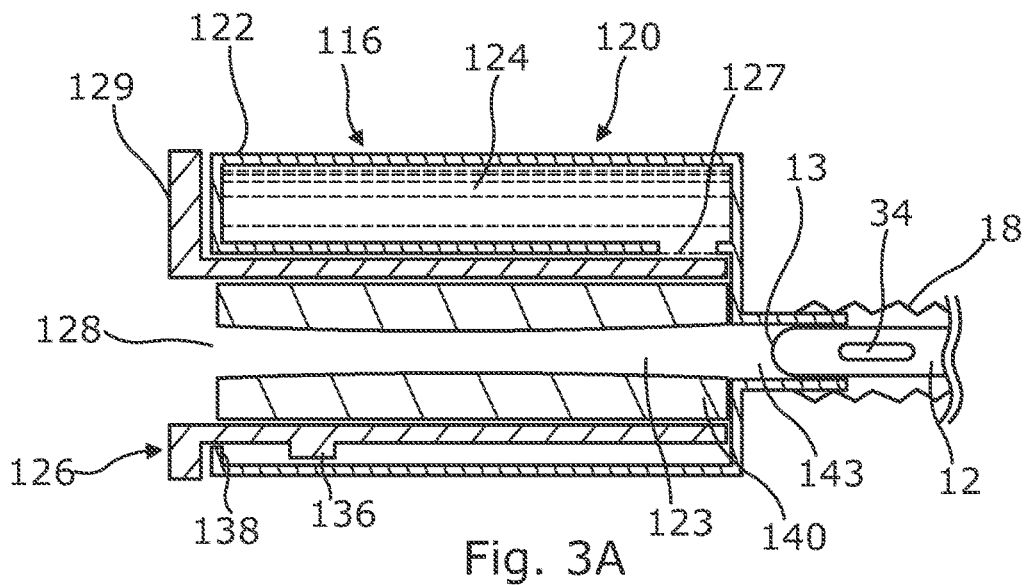
FIGS. 3A-3C are a series of cross-sectional schematic views illustrating the operational use of a third embodiment of the invention.
Figure 3B:
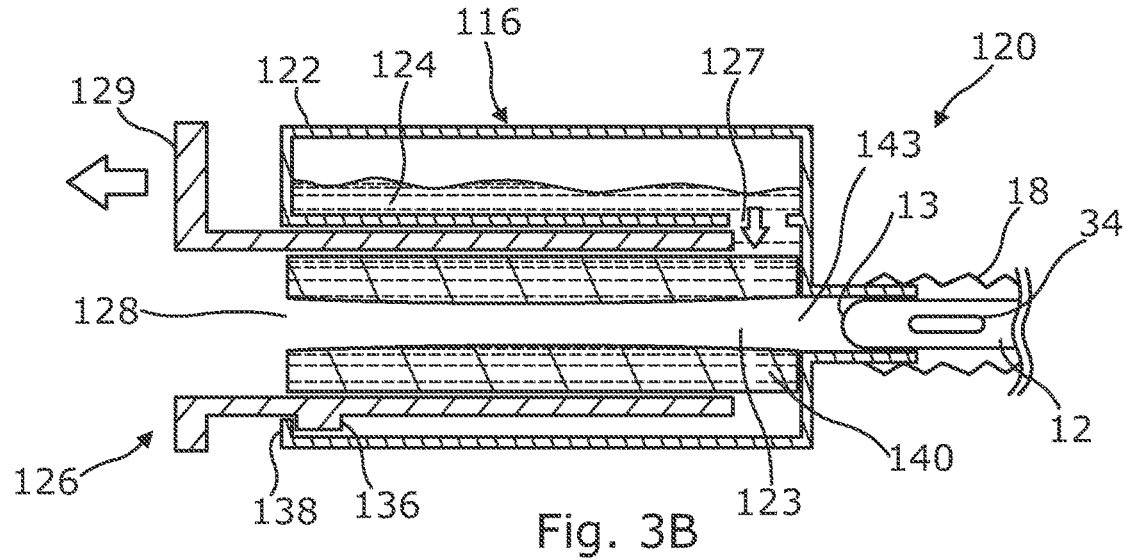
Figure 3C:
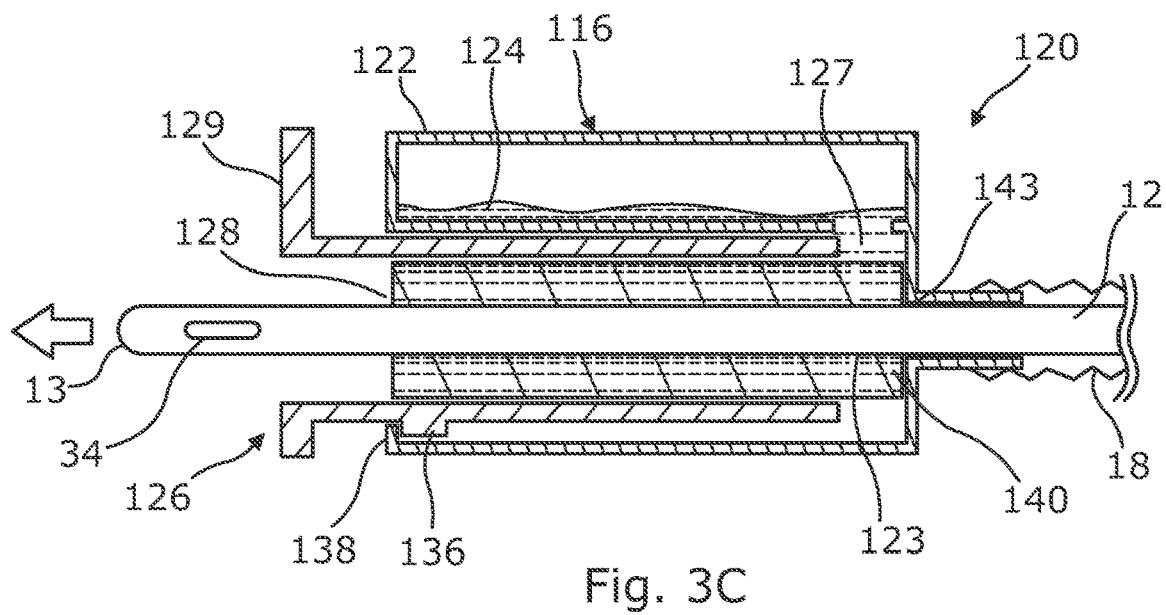

A variant of wetting mechanism 20' is shown in FIGS. 3A-3C. Specifically, these figures show a wetting mechanism 120 configured in substantially the same way as wetting mechanism 20' shown in FIGS. 2A-2C. Wetting mechanism 120 differs in that it comprises a fluid release control component in the form of a plug 126. As is described herein, the plug 126 is configured to control release of the fluid 124 from the holding chamber 122 to the wetting chamber 123, and specifically from the holding chamber 122 onto a wetting applicator in the form of foam conduit 140. The holding chamber 122 and wetting chamber 123 are fluidly connected to one another by an opening 127 in the housing 116.

The fluid 124 is released from said holding chamber 122 into the wetting chamber 123, and onto the foam conduit 140, upon movement of the plug 126. To assist with this, a lip 129 is provided at an end of the plug 126 defining an interaction point for the user, specifically for the user to grip the lip 129 to provide leverage.

Initially, the wetting mechanism 120 is provided in a first position with the plug 126 in a first position blocking the opening 127 (FIG. 3A). In order to activate the wetting mechanism 120, the plug 126 is partially displaced from (i.e. pulled out from) the wetting chamber 123 to a second position (FIG. 3B). In doing so, the plug 126 is moved to a position where the opening 127 is no longer blocked, allowing the fluid 124 to be released from the holding chamber 122 into the wetting chamber 123, and specifically onto the foam conduit 140. A notch 136 is provided on an outer circumferential surface of the plug 126 to define the extent to which the plug 126 can be removed from the wetting chamber 123. Specifically, the notch 136 provides a point of contact between the plug 126 and a circumferentially inwardly extending flange 38 at the end of the housing 116.

Subsequently, the catheter tube 12 may be moved into and through the wetting chamber 123 via the inlet 143 in the same manner as wetting mechanisms 20, 20' described above, bringing the catheter tube 12 into contact with (and apply pressure to) the foam conduit 140. This pressure causes release of the fluid 124 from the foam conduit 140, thereby wetting an outer surface of the catheter tube 12. Once the tip end 13 of the catheter tube 12 is moved beyond the lip 129 in the plug 126, and out through an outlet 128 of the housing 116, the tip end 13 then becomes exposed for insertion by the user. The housing 116 then acts as a gripping element for the user to direct the catheter tube 12, in use, as the user may then use the housing 116 to easily direct the exposed tip end 13 of the catheter tube 12 without contacting the tube 12 directly.

Advantageously, having the fluid 124 stored in a separate holding chamber 122 until (or as close as possible to) the point of use of the catheter 10 reduces the contact time of most components of the catheter 10 with the fluid 124, which may be advantageous in terms of shelf-life of the catheter 10.

FIGS. 4A-4D illustrate a further embodiment of a wetting mechanism 220 according to the invention, for wetting an outer surface of the catheter tube 12.

As with wetting mechanisms 20, 20', 120, the wetting mechanism 220 comprises a housing 216 positioned (at least initially) at a tip end 13 of the catheter tube 12. The housing 216 again includes a holding chamber 222 which contains a volume of fluid 224 therein for wetting the catheter tube 12, and a wetting chamber 223 into which the fluid 324 may be released—specifically through an opening 227 within the housing 216. The wetting chamber 223 again defines a separate portion of the housing 216 and includes a foam conduit 240 defining a channel through the wetting chamber 223 through which at least a portion of the catheter tube 12 is able to be introduced and be moved therethrough.

Wetting mechanism 220 differs in that it includes a plug 226 which is, at least initially, provided within the wetting chamber 223 and specifically within the channel defined by the foam conduit 240. In this position (FIGS. 4A and 4B), fluid 224 from the holding chamber 222 may be released through the opening 227 and on to the foam conduit 240, however, the plug 226 acts to effectively seal the wetting chamber 223 such that none of the fluid within the foam conduit 240, or indeed still within the holding chamber 222 can be released. In this position, the plug 226 also prevents the catheter tube 12 from being introduced into the wetting chamber 223. Accordingly, the plug 226 may prevent or at least reduce the likelihood of inadvertent activation of the wetting mechanism 220.

The plug 226 is configured such that it can be fully removed from the wetting chamber 223, specifically by pulling the plug 226 out through outlet 228 in the housing 216. The plug 226 is provided with an enlarged rounded end portion 229 to assist with the user gripping the plug 226. Withdrawal of the plug 226 from the wetting chamber 223 unblocks the inlet 243 (FIG. 4C). The catheter tube 12 may then be moved into and through the wetting chamber 223 via the inlet 243 in the same manner as wetting mechanisms 20, 120 described above, bringing the catheter tube 12 into contact with (and apply pressure to) the foam conduit 240. This pressure causes release of the fluid 224 from the foam conduit 140, thereby wetting an outer surface of the catheter tube 12. Once the tip end 13 of the catheter tube 12 is moved out through the outlet 228 of the housing 216, the tip end 13 then becomes exposed for insertion by the user. Again, the housing 216 acts as a gripping element for the user to direct the catheter tube 12, in use, as the user may then use the housing 216 to easily direct the exposed tip end 13 of the catheter tube 12 without contacting the tube 12 directly.

Figure 5A:
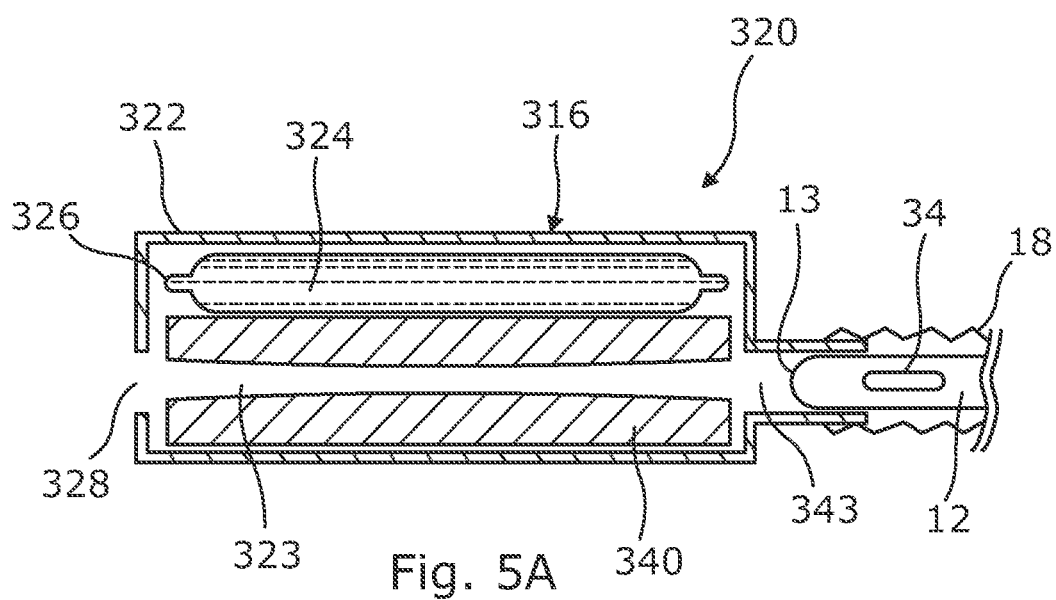
FIGS. 5A-5C are a series of cross-sectional schematic views illustrating the operational use of a fifth embodiment of the invention.
Figure 5B:
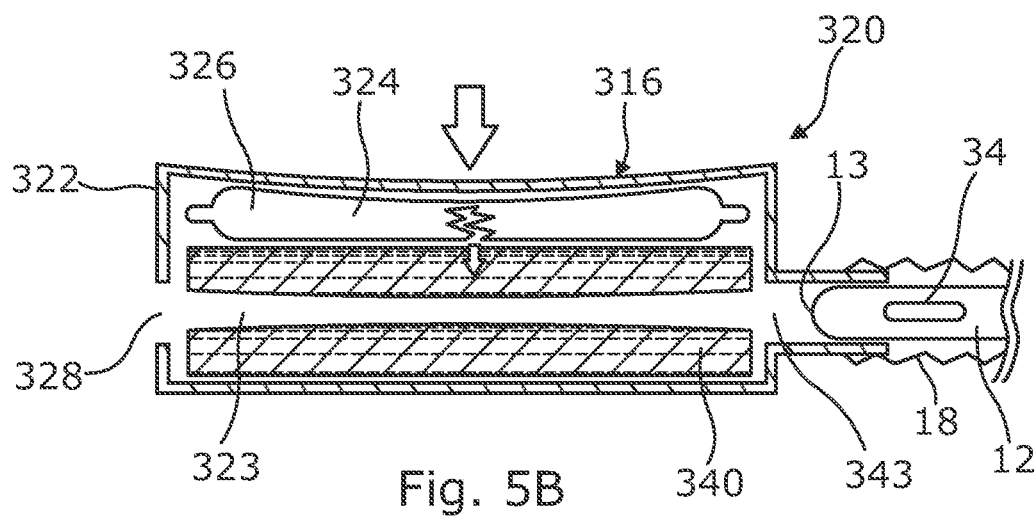
Figure 5C:
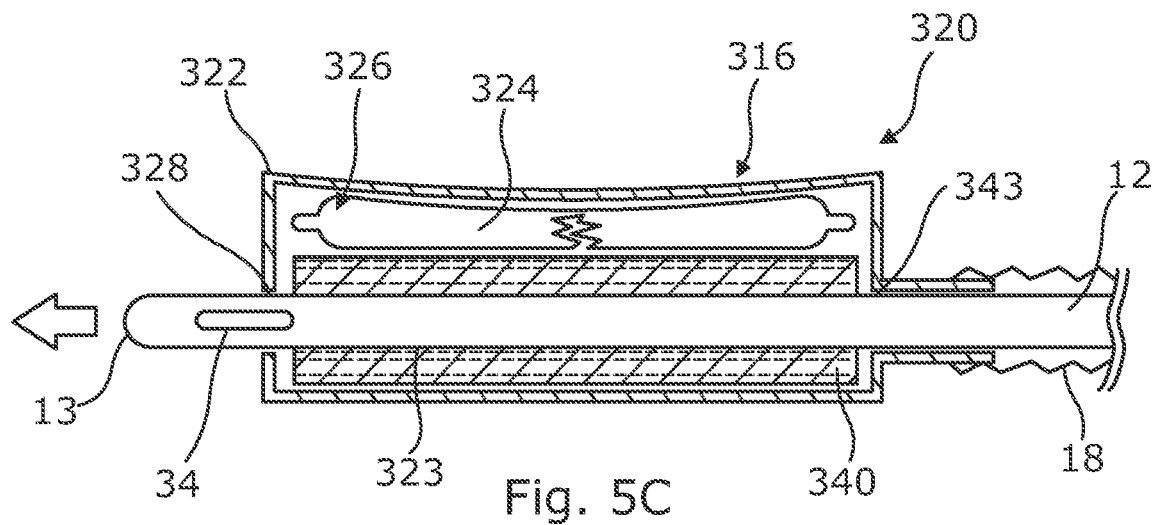

FIGS. 5A-5C illustrate a further embodiment of a wetting mechanism 320 according to the invention, for wetting an outer surface of the catheter tube 12.

As with wetting mechanisms 20, 20', 120, 220, the wetting mechanism 320 comprises a housing 316 positioned (at least initially) at a tip end 13 of the catheter tube 12. The housing 316 again includes a holding chamber 322 which contains a volume of fluid 324 therein for wetting the catheter tube 12, and a wetting chamber 323 into which the fluid 324 may be released.

Wetting mechanism 320 differs in that it includes a fluid release control component in the form of a container of fluid, specifically a sachet 326 which must be ruptured in order to release the fluid 324 therefrom and into the wetting chamber 323 and onto a wetting applicator in the form of a foam conduit 340. As with foam conduit 40, 140, 240, the foam conduit 340 is configured to hold fluid released thereon from the holding chamber 322 and is configured to control application of the fluid to the catheter tube 12, in use, as the catheter tube 12 is moved through the housing 316. As shown, the sachet 326 effectively defines the holding chamber 322. Similarly, the foam conduit 340 defines the wetting chamber 323 through which the catheter tube 12 may be moved, in use.

The sachet 326 is initially provided in the configuration shown in FIG. 5A—i.e. intact, with the fluid contained therein. In use, the sachet 326 is ruptured through a user applying an external force to the housing 316, i.e. by squeezing the housing 316 (as shown figuratively in FIG. 5B), which may be formed of a deformable material, or with a deformable region that can be squeezed. Rupture of the sachet 326 causes the fluid contained therein to be released into the wetting chamber 323, and specifically onto the foam conduit 340. As with wetting mechanisms 20, 20', 120, 220 the catheter tube 12 may then be moved through the wetting chamber 323 in contact with the foam conduit 340 and out through an outlet 328 at a distal end of the housing 316 to both wet the outer surface of the catheter tube 12 and expose the tip end 13 for insertion by the user. Again, the housing 316 acts as a gripping element for the user to direct the catheter tube 12, in use.

Figure 6:
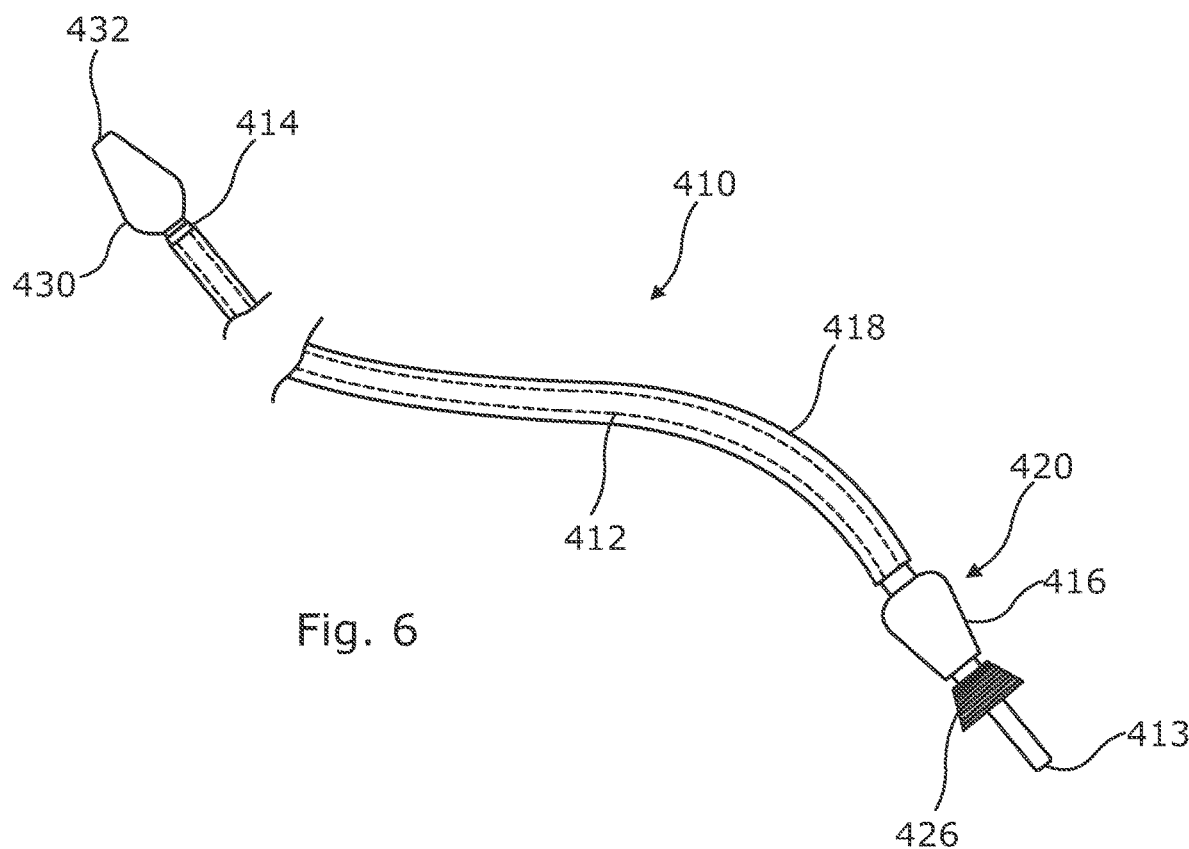
FIG. 6 is a perspective view of a sixth embodiment of the invention.
Figures 7A, 7B:
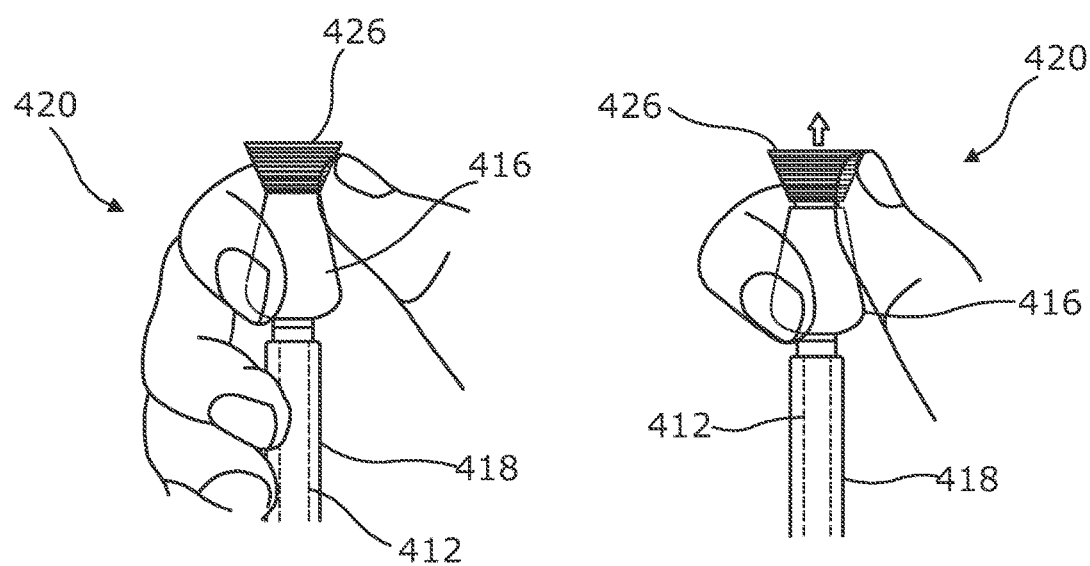
FIGS. 7A-7B are a pair of side views illustrating the operational use of the embodiment shown in FIG. 6.

FIGS. 6-7B illustrate a further embodiment of a catheter 410 and wetting mechanism 420 operable to wet a tube 412 of the catheter 410, in use.

As with catheter 10, the catheter 410 includes the catheter tube 412, with the wetting mechanism 420 provided at a tip end 413 of the catheter tube 412 and a funnel 430 at a distal end 414 of the catheter tube 412. A sleeve 418 is provided between the wetting mechanism 420 and the funnel 430, enclosing the catheter tube 12 therebetween.

The tip end 413 of the catheter 410 includes a tip for insertion of the catheter tube 412 into a canal, vessel, passageway, body cavity, etc. for removal of fluid therefrom.

Here, the catheter 410 comprises a male urinary catheter 410 with the tip configured for insertion into a male patient's bladder. The distal end 414 of the catheter tube 412 is provided within the funnel 430. Specifically, the distal end 414 of the catheter tube 412 is located within the funnel 430 and opens into the funnel 430 which defines a fluid outlet 432 which serves as an outlet for discharging fluid from within the catheter tube 412. The funnel 430 is shaped to aid the user's control over the direction of discharge of the fluid from the catheter tube 412. The catheter tube 412 itself comprises a hydrophilic coating which acts to provide a low friction outer surface of the catheter tube 412 upon application of a wetting fluid.

The wetting mechanism 420 is similar in configuration to wetting mechanism 120 described herein, and may be of the nature of, with the same features as the embodiment shown in FIGS. 3A-3C. It includes a housing 416 positioned (at least initially) at the tip end 413 of the catheter tube 412. The housing 416 includes a holding chamber (not shown) which contains a volume of fluid therein for wetting the catheter tube 412. In use, and as is described herein, the fluid may be released from said holding chamber into a wetting chamber (not shown) of the housing 416 under the operation of a plug 426. As with wetting mechanism 120, by releasing the fluid into the wetting chamber, and specifically onto a wetting applicator in the form of a foam conduit (not shown), and then subsequently moving the catheter tube 412 through the wetting chamber in contact with the foam conduit, an outer surface of the catheter tube 412 may be wetted using the fluid. The plug 426 is moveable from the position shown in FIG. 7A (a first position) to the position shown in FIG. 7B (a second position) to release the fluid from the holding chamber. Specifically, movement of the plug 426 between these positions may unblock an opening within the housing 416 or rupture a sachet, for example, to allow for the fluid to be released from the holding chamber into the wetting chamber and into/onto the foam conduit for subsequent application to the catheter tube 412.

In this embodiment, the plug 426 comprises a conical cross section, with a ridged exterior surface defining an interaction surface for the user. The housing 416 is also substantially conical in profile, and is positioned in such a way to define an hourglass-shaped configuration of the housing 416 and plug 426. This arrangement is particularly beneficial as it may allow for operation of the plug 426 using only one hand, as shown in FIGS. 7A and 7B. Specifically, and as shown in these Figures, the user may grip the housing 416 and plug 426 between their thumb and forefinger, before using their thumb to push or "pop" the plug 426 upwards (in the orientation shown in the Figures) to release the fluid. Moreover, the conical plug 426 has a cup like end, which eases location of the housing 416 over the tip of the penis to aid insertion of the catheter tube 412 into the urethra, in use.

Figure 8A:
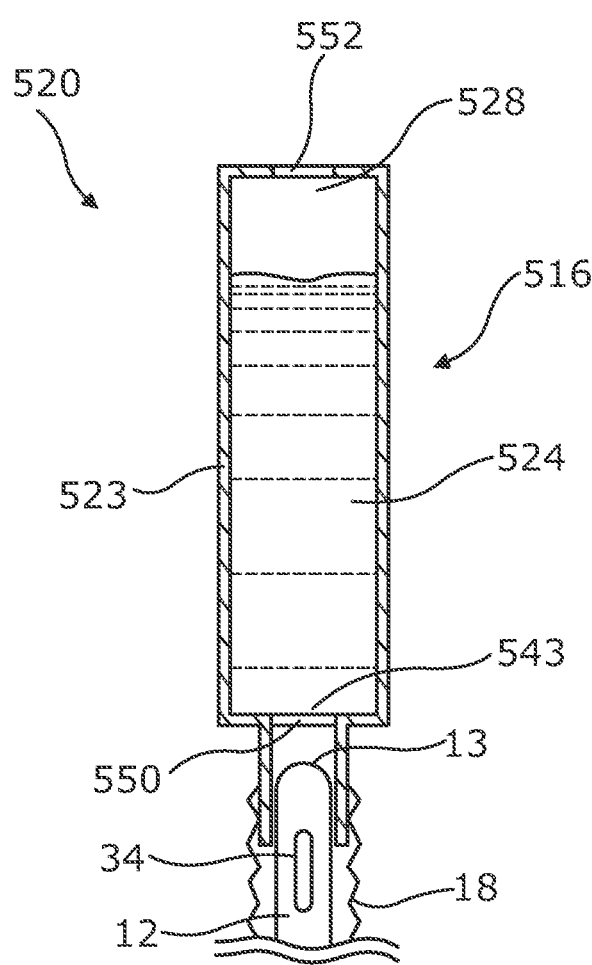
FIGS. 8A-8B are a series of cross-sectional schematic views illustrating the operational use of a seventh embodiment of the invention.
Figure 8B:
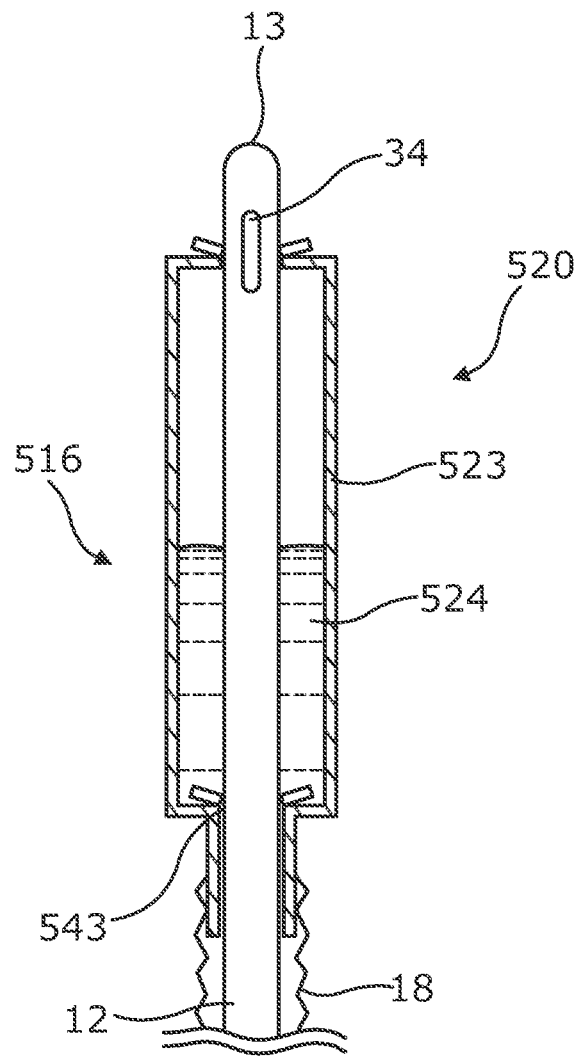

FIGS. 8A-8B illustrate a further embodiment of a wetting mechanism 520 for use in wetting catheter tube 12 of catheter 10.

The wetting mechanism 520 includes a tubular housing 516 positioned (at least initially) at a tip end 13 of the catheter tube 12. The housing 516 includes an inlet 543 and outlet 528 through which the catheter tube 12 may be moved, in use. Specifically, the catheter tube 12 may be introduced into the housing 516 through the inlet 543, and may be moved out of the housing 516 through the outlet 528 to expose the tip end 513 thereof, i.e. for subsequent insertion into the urethra.

Wetting mechanism 520 differs from the mechanisms described hereinabove in that it does not include a wetting applicator within the wetting chamber 523. Rather, the wetting fluid 524 is contained within the wetting chamber 523 itself, and the wetting fluid 524 is applied to catheter tube 12, in use, as the catheter tube 12 is moved through the wetting chamber 523.

The wetting chamber 523 defines a channel through the housing 516 through which at least a portion of the catheter tube 12 is able to be introduced and be moved therethrough. The channel is defined between the inlet 543 and outlet 528 of the housing 516. When moving through the channel, the catheter tube 12 is brought into contact with wetting fluid 524 held within the wetting chamber 523 thereby coating an exterior surface of the tube 12 with the wetting fluid 524 as it is moved through the wetting chamber 523.

The wetting mechanism 520 includes an inlet valve 550 provided at the inlet 543 and an outlet valve 552 provided at the outlet 528. The inlet and outlet valves 550, 552 advantageously seal the inlet and outlet 542, 528 preventing the wetting fluid 524 from leaking from the wetting chamber 523. The valves 550, 552 further allow for the passage of the catheter tube 12 through the wetting chamber 523. Specifically, the inlet valve 550 is configured to allow the catheter tube 12 to be moved therethrough to introduce the catheter tube 12 into the wetting chamber 523 of the housing 516. Similarly, the outlet valve 552 is configured to allow the catheter tube 12 to be moved therethrough to expose the catheter tube 12 for subsequent use/insertion by the user.

As with the other embodiments described hereinabove, once the tip end 13 of the catheter tube 12 is moved out through the outlet 528 of the housing 516, the tip end 13 then becomes exposed for insertion by the user, and the housing 516 then acts as a gripping element for the user to direct the catheter tube 12, in use. The user may then advantageously use the housing 16 to easily direct the exposed tip end 13 of the catheter tube 12 without contacting the tube 12 directly.

In a variant, the wetting applicator (where present) may comprise a wicking material. The wicking material may be configured to provide a wicking action between the holding chamber (e.g. holding chambers 22, 122, 222, 322) and the wetting chamber (e.g. wetting chambers 23, 123, 223, 323), enabling the transfer of the fluid from the holding chamber into the wetting chamber for subsequent application to the catheter tube. This is enabled in the illustrated embodiments, for example, by having the wetting fluid 24, 124, 224, 324 in contact with the wetting applicator, or indeed by releasing the wetting fluid onto and in contact with the wetting applicator—e.g. through use of a fluid release control component.

In a further variant, the wetting applicator (where present) may comprise a baffle arrangement which defines a plurality of subregions of the wetting applicator each configured to hold a portion of the fluid held within the wetting applicator. For example, the baffle arrangement may define a plurality of subregions within the housing 16, 116, 216, 316, 416 e.g. within the wetting chamber 23, 123, 223, 323 of the housing 16, 116, 216, 316, 416 in which the fluid may reside and or be released into, e.g. from the holding chamber 22, 122, 222, 322.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The one or more embodiments are described above by way of example only. Many variations are possible without departing from the scope of protection afforded by the appended claims.

The invention claimed is:

1. A wetting mechanism for wetting a tube of a male urinary catheter, the wetting mechanism comprising:
a housing forming a gripping element for the catheter, the housing being configured to be positioned initially at or proximal to a tip end of the catheter tube;
wherein the housing comprises a wetting chamber, wherein at least a portion of the catheter tube is able to move through the wetting chamber; and
wherein the wetting mechanism comprises a wetting applicator positioned within the wetting chamber, wherein the wetting applicator is configured to hold fluid within the wetting applicator, and wherein the wetting applicator is configured to release said fluid to wet the catheter tube upon movement of the tube through the wetting chamber.

2. A wetting mechanism as claimed in claim 1, wherein the wetting applicator comprises a flexible, compressible and/or resilient material and is deformable under the application of a force thereto, and wherein deformation of the wetting applicator causes release of fluid held therein.

3. A wetting mechanism as claimed in claim 1, wherein the wetting applicator comprises a baffle arrangement.

4. A wetting mechanism as claimed in claim 3, wherein the baffle arrangement defines a plurality of subregions of the wetting applicator each configured to hold a portion of the fluid held within the wetting applicator.

5. A wetting mechanism as claimed in claim 4, wherein the baffle arrangement defines a plurality of subregions within the wetting chamber in which the fluid may reside and/or be released into.

6. A wetting mechanism of claim 1, wherein the housing comprises a holding chamber containing a volume of wetting fluid therein, and wherein the wetting chamber is fluidly connected or connectable to the holding chamber.

7. A wetting mechanism as claimed in claim 6, comprising a fluid release control component operable, in use, to control release of the fluid from the holding chamber into the wetting chamber.

8. A wetting mechanism as claimed in claim 7, wherein the fluid release control component is operable to control release of the fluid from the holding chamber onto and/or into the wetting applicator.

9. A wetting mechanism as claimed in claim 8, wherein the fluid release control component comprises a moveable plug, moveable between a first position wherein it prevents release of the fluid from the holding chamber to the wetting chamber and/or the wetting applicator, and a second position wherein it allows release of the fluid from the holding chamber to the wetting chamber and/or the wetting applicator, wherein the plug is linearly moveable or is rotatable between first and second positions.

10. A wetting mechanism as claimed in claim 9, wherein movement of the plug between first and second positions exposes or otherwise unblock one or more openings within the housing between the holding chamber and the wetting chamber, thereby releasing fluid from within the holding chamber and into the wetting chamber and/or into or onto the wetting applicator.

11. The wetting mechanism as claimed in claim 1, wherein the housing further comprises an outlet, and wherein the tip end of the catheter tube is exposed outside of the housing through the outlet upon the movement of the tube through the wetting chamber.

12. The wetting mechanism as claimed in claim 11, wherein the gripping element is operable to direct the exposed tip end of the catheter tube when grasped by a user.

13. A wetting mechanism for wetting a tube of a male urinary catheter, the wetting mechanism comprising:
a housing forming a gripping element for the catheter, the housing being configured to be positioned initially at or proximal to a tip end of the catheter tube;
wherein the housing comprises a wetting chamber;
wherein at least a portion of the catheter tube is operable to move through the wetting chamber;
wherein the housing further comprises a fluid release control component at least partially surrounding a wetting applicator positioned within the wetting chamber; and
wherein the wetting mechanism is configured such that the catheter tube is wetted with wetting fluid contained within the housing upon movement of the tube through the wetting chamber.

14. A wetting mechanism as claimed in claim 13, wherein the wetting fluid is contained within a holding chamber within the housing, the fluid release control component operable to fluidly connect the holding chamber and the wetting chamber.

15. A wetting mechanism as claimed in claim 14, wherein the housing comprises an opening or a port located between the holding chamber and the wetting chamber, and through which the wetting fluid may flow; and
wherein the opening or port is configured such that the rate at which the wetting fluid may flow therethrough is limited by the surface tension of the wetting fluid.

16. A system comprising the wetting mechanism of claim 13, the system further comprising:
a catheter tube having a tip end and a distal end; and
a funnel provided at a distal end portion of the catheter tube, with the wetting mechanism and funnel being separate components coupled via the catheter tube, wherein, the wetting mechanism is operably coupled to the tip end of the catheter tube for wetting the catheter tube, in use.

17. A system according to claim 16 wherein the catheter comprises a sleeve formed of a film of plastics material positioned about the catheter tube, defining an internal volume about at least a portion of the catheter tube; the sleeve being coupled at a first end to the wetting mechanism and at a second, opposing end to the funnel.

18. A system according to claim 16, further comprising a sealed package, wherein the wetting mechanism is operably coupled at or proximal to the tip end of the catheter tube within the sealed package.

19. The system according to claim 16, wherein the tip end of the catheter tube is exposed through an outlet of the housing and extends beyond a flange of the fluid release control component upon the movement of the catheter tube.

20. The system according to claim 19, wherein the gripping element is operable to direct the exposed tip end of the catheter tube when grasped by a user.

* * * * *